(12) United States Patent
Razavi et al.

(10) Patent No.: US 9,095,262 B2
(45) Date of Patent: Aug. 4, 2015

(54) GUIDED ABLATION DEVICES, SYSTEMS, AND METHODS

(76) Inventors: Mehdi Razavi, Houston, TX (US); Christopher Alex Arevalos, Houston, TX (US)

( * ) Notice: Subject to any disclaimer, the term of this patent is extended or adjusted under 35 U.S.C. 154(b) by 728 days.

(21) Appl. No.: 13/344,100

(22) Filed: Jan. 5, 2012

(65) Prior Publication Data
US 2012/0197100 A1  Aug. 2, 2012

Related U.S. Application Data (60) Provisional application No. 61/429,809, filed on Jan. 5, 2011.

(51) Int. Cl.
*A61B 5/042* (2006.01)
*A61B 18/08* (2006.01)
(Continued)

(52) U.S. Cl.
CPC ........... *A61B 5/0422* (2013.01); *A61B 1/00158* (2013.01); *A61B 5/062* (2013.01);
(Continued)

(58) Field of Classification Search
CPC .. A61B 1/00158; A61B 5/0422; A61B 5/062; A61B 5/6858; A61B 18/1492; A61B 2018/00577; A61B 2018/0016; A61B 2018/00267; A61B 2018/00351; A61B 2018/00375; A61B 2018/00839; A61B 2019/2253; A61B 2019/2257; A61B 2017/00053
USPC .......... 600/373–375, 393, 424, 431, 433, 435
See application file for complete search history.

(56) References Cited

U.S. PATENT DOCUMENTS 5,429,131 A * 7/1995 Scheinman et al. .......... 600/374
5,895,404 A    4/1999 Ruiz
(Continued)

FOREIGN PATENT DOCUMENTS

WO   2008150796   11/2008
WO   2009086269   9/2009
WO   2010014420   4/2010

OTHER PUBLICATIONS

Bard Electrophysiology, "Ablation Redefined, Bard HD Mesh Ablator Catheter, A Complete AF Procedural Solution," 2008, 4 pages.
(Continued)

*Primary Examiner* — Lee S Cohen
*Assistant Examiner* — Erin M Cardinal
(74) *Attorney, Agent, or Firm* — Trop, Pruner & Hu, P.C.

(57) ABSTRACT

An embodiment of the invention includes a system for the guidance of a catheter to different regions of tissue (e.g., cardiac tissue) for therapy (e.g., ablation therapy). A plurality of electrodes, such as an array of electrodes, may be configured to perform various tasks. First, some electrodes may measure cardiac polarization. Second, some electrodes may function as magnets (e.g., electromagnets) that guide a separate ablation catheter towards the electromagnetic electrodes. These electromagnetic electrodes may be positioned adjacent tissue that is now recognized (possibly due to the electrodes that measure cardiac polarization) as being in need of ablation therapy. Thus, the electromagnetic electrodes may cooperate with an ablation catheter to render a system with magnetic guidance capabilities using intracardiac magnetic field generation. The system may control electromagnetic forces from the array of electrodes to guide the ablation catheter tip to the desired therapy location. Other embodiments are described herein.

19 Claims, 9 Drawing Sheets

(51) Int. Cl.

| | | |
|---|---|---|
| *A61M 25/088* | (2006.01) | |
| *A61B 1/00* | (2006.01) | |
| *A61B 5/06* | (2006.01) | |
| *A61B 18/14* | (2006.01) | |
| *A61M 25/01* | (2006.01) | |
| *A61B 17/00* | (2006.01) | |
| *A61B 5/00* | (2006.01) | |
| *A61B 18/00* | (2006.01) | |
| *A61B 19/00* | (2006.01) | |

(52) U.S. Cl.
CPC ........ *A61B18/1492* (2013.01); *A61M 25/0127* (2013.01); *A61M 25/0158* (2013.01); *A61B 5/6858* (2013.01); *A61B 2017/00053* (2013.01); *A61B 2018/00267* (2013.01); *A61B 2018/00279* (2013.01); *A61B 2018/00351* (2013.01); *A61B 2018/00357* (2013.01); *A61B 2018/00839* (2013.01); *A61B 2019/2253* (2013.01); *A61B 2019/2257* (2013.01)

(56) References Cited

U.S. PATENT DOCUMENTS

| | | | |
|---|---|---|---|
| 6,332,089 B1* | 12/2001 | Acker et al. | 600/424 |
| 6,379,319 B1* | 4/2002 | Garibotto et al. | 600/585 |
| 6,540,657 B2 | 4/2003 | Cross, III et al. | |
| 6,599,288 B2 | 7/2003 | Maguire et al. | |
| 7,280,863 B2 | 10/2007 | Shachar | |
| 7,769,427 B2 | 8/2010 | Shachar | |
| 2002/0087044 A1* | 7/2002 | Cross et al. | 600/9 |
| 2007/0106289 A1 | 5/2007 | O'Sullivan | |
| 2007/0167740 A1* | 7/2007 | Grunewald et al. | 600/424 |
| 2008/0208182 A1* | 8/2008 | Lafontaine et al. | 606/21 |
| 2010/0079158 A1 | 4/2010 | Bar-Tal et al. | |
| 2010/0191232 A1 | 7/2010 | Boveda | |
| 2011/0276075 A1* | 11/2011 | Fung et al. | 606/185 |

OTHER PUBLICATIONS

Wikipedia, "Stereotaxis," Nov. 23, 2010, 8 pages.

* cited by examiner

Fig 18 ing some electrodes with horizontal windings and some electrodes with vertical windings that cooperate to drive a catheter in a uniform direction in an embodiment of the invention.
GUIDED ABLATION DEVICES, SYSTEMS, AND METHODS This application claims priority to U.S. Provisional Patent Application No. 61/429,809, filed on Jan. 5, 2011 and entitled "Guided Ablation Devices, Systems, and Methods", which is hereby incorporated by reference.

BACKGROUND

Current cardiac ablation therapy typically uses an ablation catheter. This catheter is often navigated around the heart so ablation can be delivered at targeted locations. Such navigation can be complex and time consuming. Systems geared toward facilitating this process have been described and are currently in practice. For example, remote magnetic navigation (RMT) uses external magnetic fields to guide the ablation catheter (which is magnetically active) towards a location. However, RMT has limitations. First, the operating room has to be specifically configured to create the external magnetic field (which can be very expensive). This may involve providing operating room space for magnets and the like. Second, the target location is defined by the operator without any specific electrophysiologic properties. For example, unless the operator elects to approach a location where intracardiac electrodes are already in place, the external magnetic field merely guides the catheter but does not provide electrophysiologic recordings. Those recordings, if used, must be supplied from another source.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact.

An embodiment of the invention includes a system for the guidance of a catheter to different regions of tissue (e.g., cardiac tissue) for therapy (e.g., ablation therapy). A plurality of electrodes, such as an array of electrodes, may be configured to perform various tasks. First, some of the electrodes may measure cardiac polarization. Second, some of the electrodes may function as magnets (e.g., electromagnets) that guide a separate ablation catheter towards the electromagnetic electrodes. These electromagnetic electrodes may be positioned adjacent tissue that is now recognized (possibly due to the electrodes that measure cardiac polarization) as being in need of ablation therapy. Some electrodes may perform both functions. Thus, the electromagnetic electrodes may cooperate with an ablation catheter to render a system with magnetic guidance capabilities using intracardiac magnetic field generation. The system may control electromagnetic forces from the array of electrodes to guide the ablation catheter tip to the desired therapy location. The electromagnetic forces may be controlled by changing the geometries and/or electromagnetic properties of the electrode array to guide or otherwise navigate a catheter within the cardiac chamber.

Figure 1:
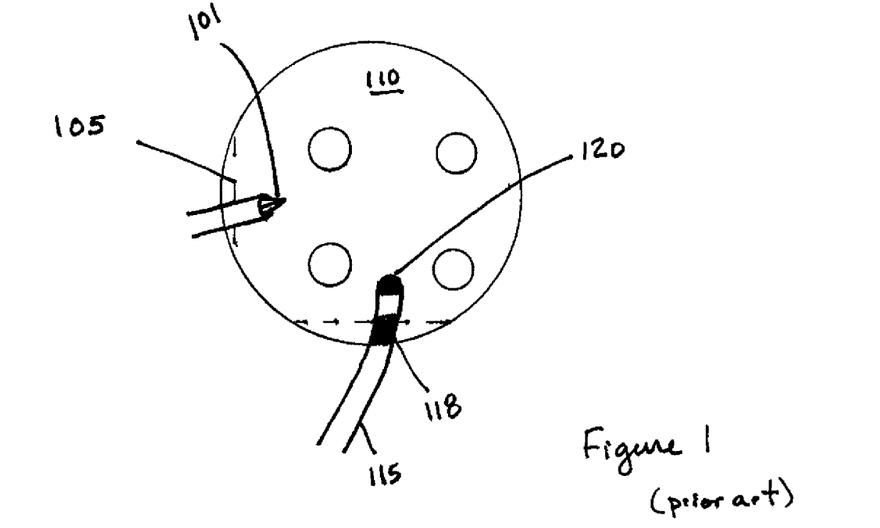
FIGS. 1-2 include depictions of the left atrium with a basket catheter and ablation catheter.
Figure 2:
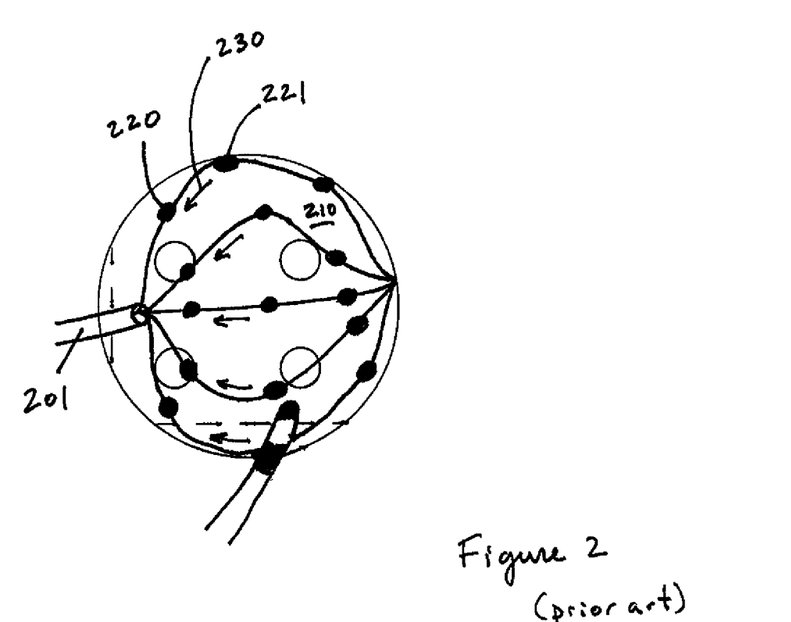

In FIG. 1 basket catheter 101 is inserted, across septum 105, into left atrium 110. Ablation catheter 115 is also included in the left atrium. As will be explained more fully below, the ablation catheter may include ablation tip 120 and magnet 118 including a ferromagnetic material. In FIG. 2, the basket catheter is deployed and electrophysiologic mapping is conducted. Specifically, electrodes 220, 221 in the electrode array of catheter 201 measure polarization wave 230 that progresses within atrium 210. (Other electrodes are included in FIG. 2 and are suitable for transmitting polarizations but are not labeled for purposes of clarity.) Electrodes 220, 221 record signals and then transmit current (Ip) 230 along the catheter to signal processing equipment (not shown). As a result, an area of problematic tissue may be located. For example, an area of tissue responsible for a reentrant circuit may be located.

Figure 8:
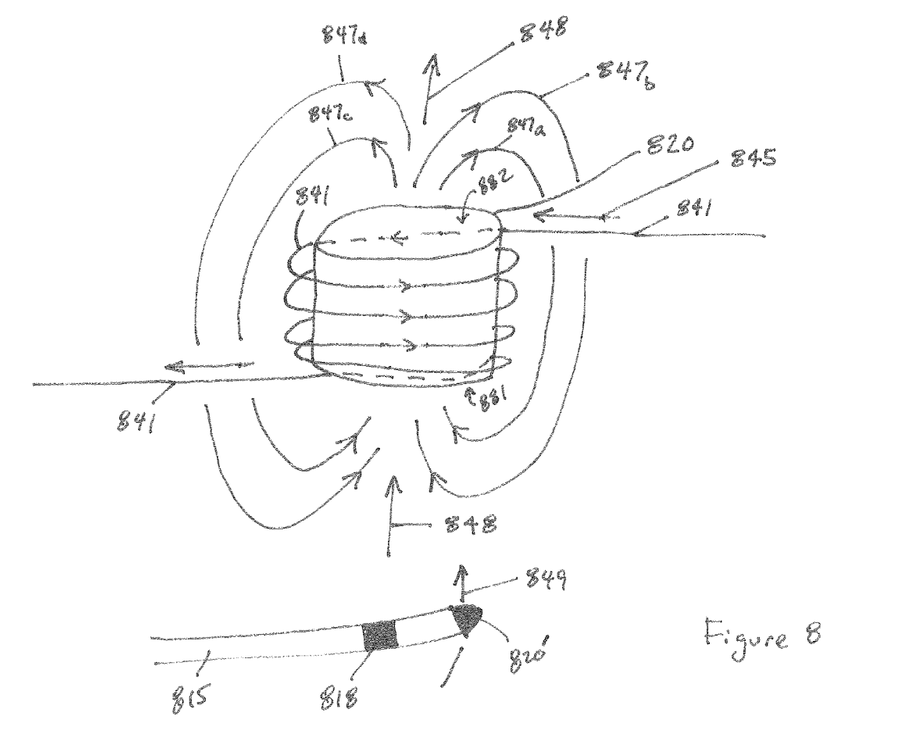

FIG. 8 includes electrode 820 (which is comparable to electrode 220 included in the electrode array of FIG. 2) that may be used for electrophysiological signal mapping. However, the electrode may also be used for electromagnetic guidance. Specifically, electrode 820 is included within or coupled to winding 841. The winding may include, for example, a 45 AWG copper core magnet wire with a polyuride coating. Wire 841 may be wrapped around electrode 820 approximately 45 times (which is not shown for purposes of clarity). As a result, sending up to 1 ampere (amp) of current through wire 841 creates approximately 0.07 Tesla of magnetic force. If the electrode is located near tissue that is a candidate for ablation, the 0.07 Tesla force may be used to attract a magnet located on an ablation catheter. The direction of the magnetic force is a function of how the wire is wound and the direction the current is sent (i.e., is the current sent clockwise or counter clockwise through the winding).

As seen in FIG. 8, and as dictated by the "right hand rule" of electromagnetics, various fields of magnetic force 847a, 847b, 847c, 847d are generated. Due to the direction of the winding and current flow, which is counter clockwise and horizontal in this example, a sum or net force 848 based on the fields is generated and applied "upwards" based on the context of the FIG. 8. Magnet 818 on a catheter, such as but not limited to ablation catheter 815, will be guided in direction 849 based on net force 848, which is the summed force of magnetic force 847a, 847b, 847c, 847d.

Figure 3:
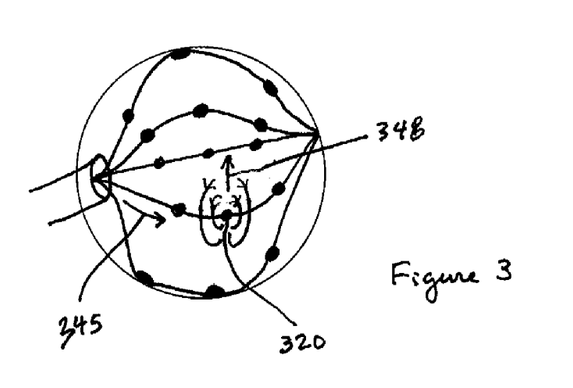
FIG. 3 includes a basket catheter in an embodiment of the invention.

FIG. 3 shows how current Im 345 may be sent to electrode 320 in an electrode array (electrode 320 is comparable to electrode 820 of FIG. 8). Im 345 is sent through the winding (not shown) as described above to generate desired attractive electromagnetic force 348. This is discussed in greater detail with, for example, FIGS. 4 and 6.

Figure 4:
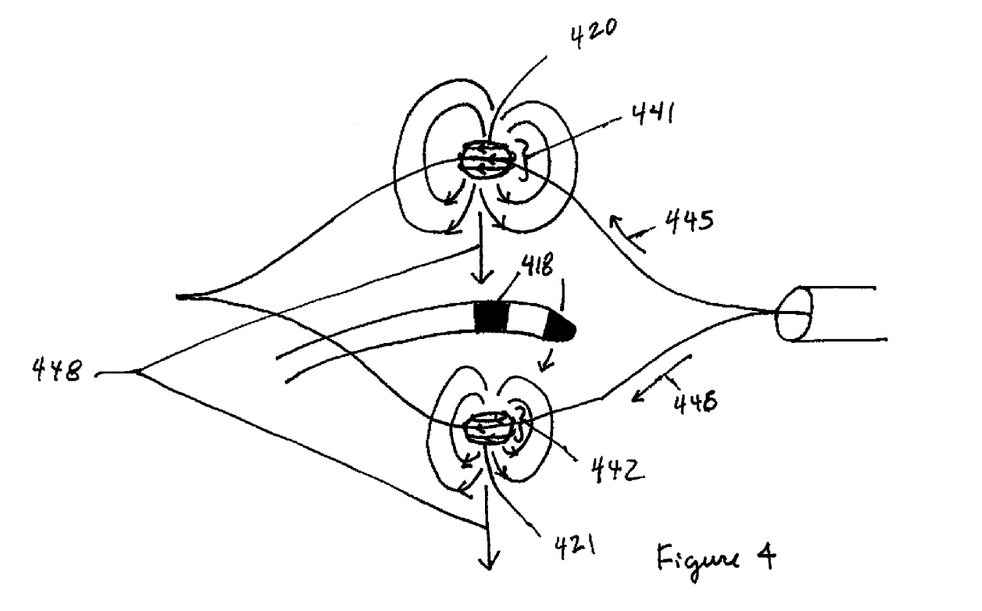
FIGS. 4-5 and 8 include electrodes with "horizontal" windings that direct an ablation catheter in embodiments of the invention.
Figure 5:
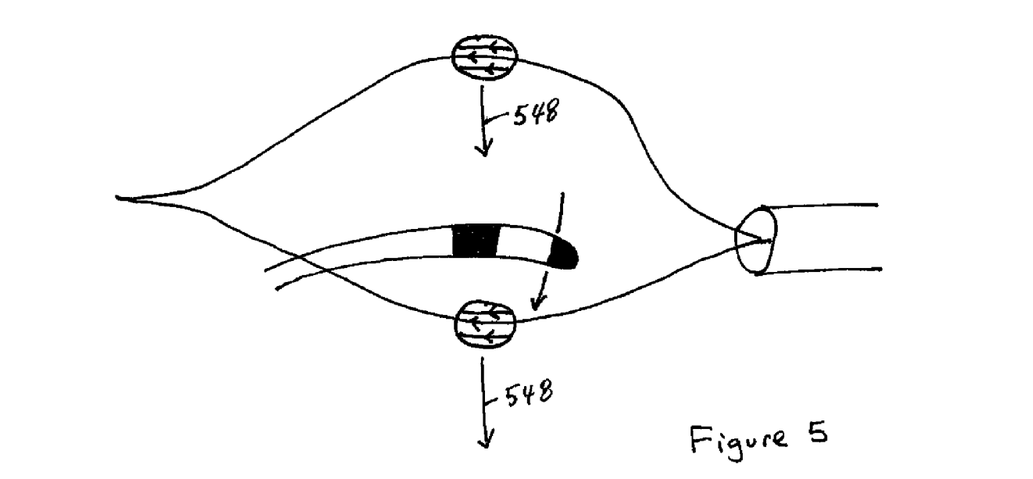

FIG. 4 illustrates how Im may be sent to multiple electrodes 420, 421. Specifically, Im1 445 is sent to electrode 420 and Im2 446 is sent to electrode 421. Considering Im1 and Im2 are both sent from the proximal end of the catheter, and further considering that windings 441, 442 are both wound "horizontally" and clockwise about electrodes 420, 421, the resultant electromagnetic forces for both electrodes 420, 421 create net force 448 that drives magnet 418 of the ablation catheter towards electrode 421 and away from electrode 420. FIG. 5 illustrates this concept more clearly by showing only net force 548 but not the individual electromagnetic fields of FIG. 4.

Figure 6:
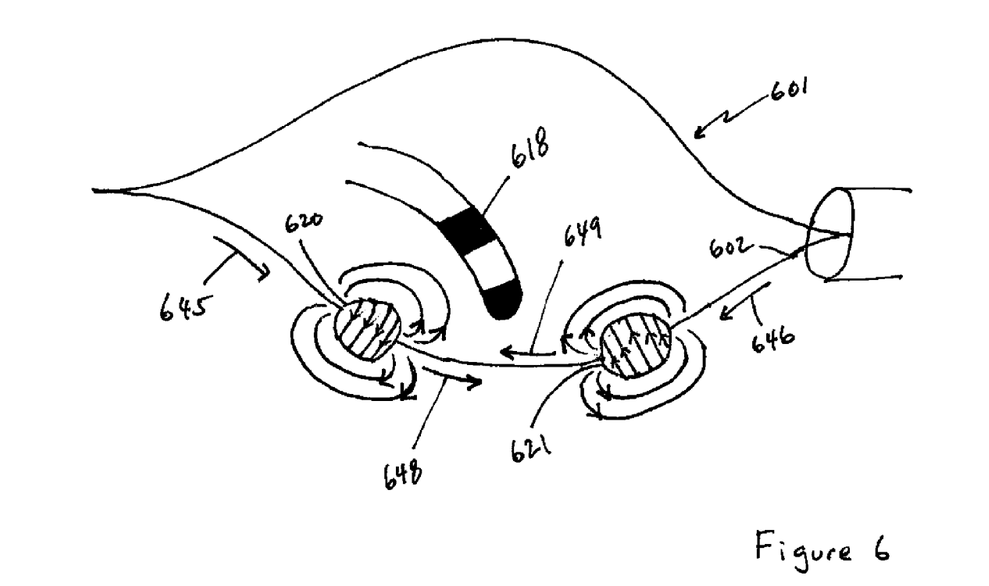
FIGS. 6-7 include electrodes with "vertical" windings that direct an ablation catheter in embodiments of the invention.
Figure 7:
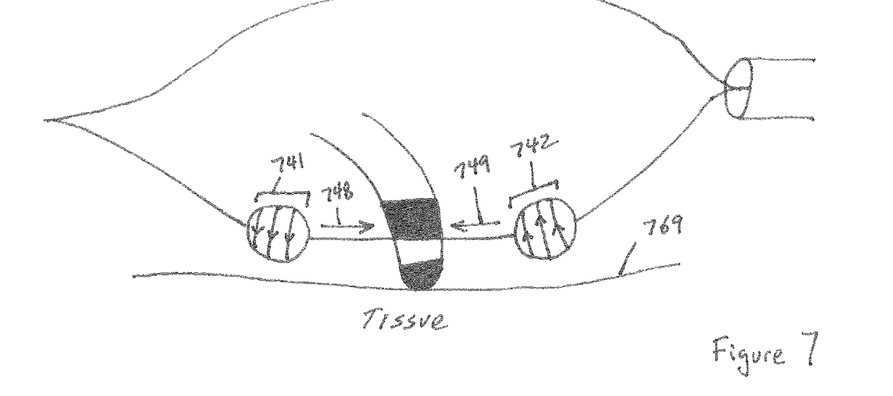

FIG. 6 illustrates another way Im may be sent to multiple electrodes. Specifically, Im1 645 is sent to electrode 620 and Im2 646 is sent to electrode 621. Electrodes 620, 621 are located on single spine 602 of basket catheter 601. Considering windings for electrodes 620, 621 are wound "vertically" and in opposite directions (i.e., current is sent clockwise for electrode 620 and current is sent counterclockwise for electrode 621) about the corresponding electrodes, the resultant electromagnetic forces 648, 649 respectively for electrodes 620, 621 create a net force that drives magnet 618 of the ablation catheter to a location between electrodes 620, 621. FIG. 7 more clearly illustrates this concept while showing only forces 748, 749 and windings 741, 742 but not the individual electromagnetic fields of FIG. 6. In FIG. 7, the ablation catheter delivers ablative energy to tissue 769 to ablate the tissue.

Figure 9:
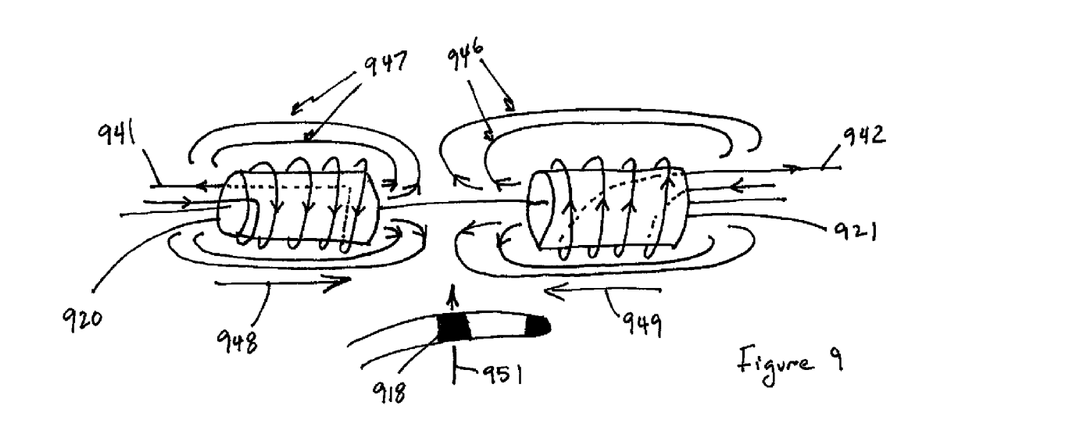
FIG. 9 includes multiple electrodes with vertical windings in an embodiment of the invention.

As seen in FIG. 9, and as dictated by the "right hand rule" of electromagnetics, various fields of magnetic force 947, 946 are respectively generated for electrodes 920, 921 (which are comparable to electrodes 620, 621 of FIG. 6). Due to the direction of the opposite vertical windings and current paths 941 (clockwise), 942 (counter clockwise), opposing sum or net forces 948, 949 are generated to a location in between electrodes 920, 921. As a result, magnet 918 on the ablation catheter is attracted along line 951 to the location between electrodes 920, 921.

Figure 10:
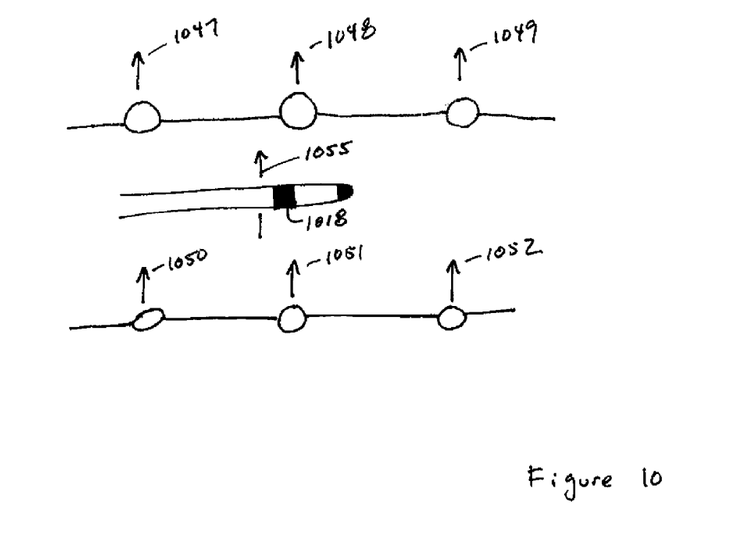
FIG. 10 includes multiple struts with multiple electrodes cooperating to drive a catheter in a direction in an embodiment of the invention.
Figure 11:
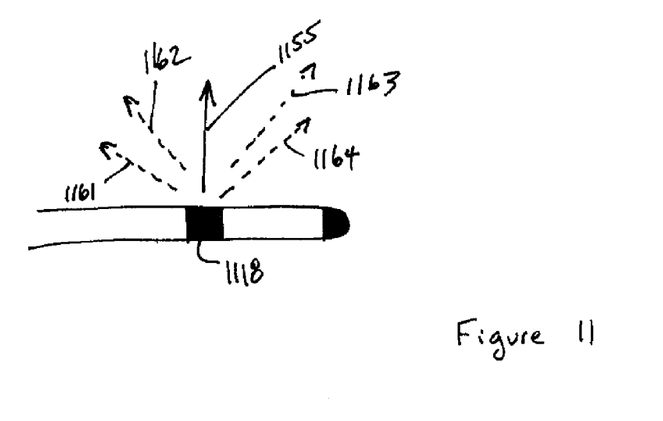
FIG. 11 includes an electrode being driven by a summed force in an embodiment of the invention.

FIG. 10 shows in greater detail how various electromagnetic moments 1047, 1048, 1049, 1050, 1051, 1052 from multiple electrodes may be summed to produce single summed moment 1055 to guide ablation catheter magnet 1018. FIG. 11 shows the same concept with a focus taken from the perspective of magnet 1118 on the ablation catheter. For instance, the ablation catheter magnet 1118 is subjected to various forces 1161, 1162, 1163, 1164 that result in a net force 1155 based on a sum of forces 1161, 1162, 1163, 1164.

Figure 12:
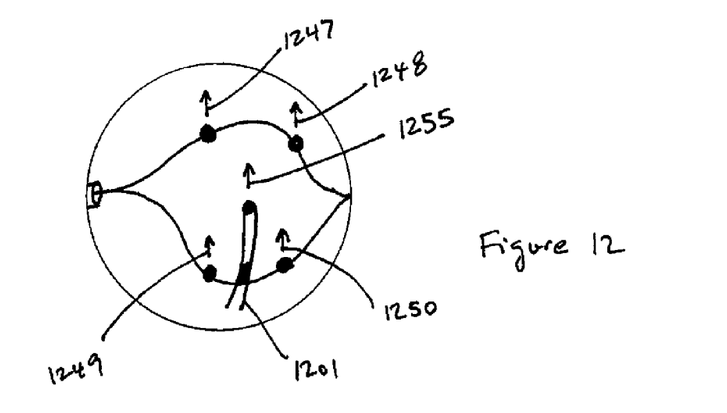
FIG. 12 includes a left atrium with multiple electrodes on a basket catheter driving a catheter in a uniform direction in an embodiment of the invention.
Figure 13:
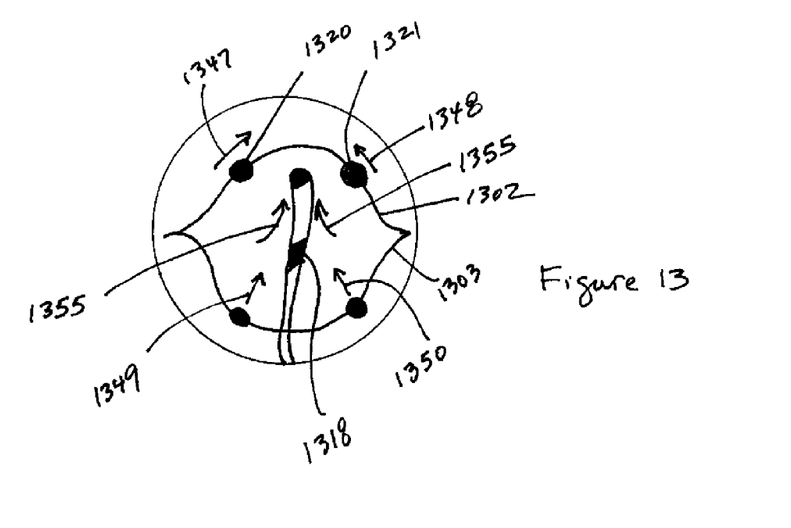
FIG. 13 includes a left atrium with a basket catheter including some electrodes with horizontal windings and some electrodes with vertical windings that cooperate to drive a catheter in a uniform direction in an embodiment of the invention.

FIGS. 12 and 13 show the above concepts from a more distant perspective of the left atrium. In FIG. 12 various electrodes are associated with moments 1247, 1248, 1249, 1250 to generate summed force 1255 on catheter 1201. Catheter 1201 may or may not be an ablation catheter. As described below, catheter 1201 may have magnetic qualities based on magnetic paint, inserts, electrodes, and the like. In FIG. 13 moments 1347, 1348 are associated with windings (not shown for purposes of clarity) that are vertical with current supplied opposite one another (clockwise versus counter clockwise) to generated opposing forces 1347, 1348 that are generally collinear (based on vertical nature of winding) with strut 1302. Moments 1349, 1350 are associated with windings (not shown for purposes of clarity) that are horizontal with current supplied similar to one another (both clockwise) to generated similarly aligned forces 1349, 1350 that are generally orthogonal (based on horizontal nature of winding) with strut 1303. The net result of both collinear moments 1347, 1348 and orthogonal moments 1349, 1350 are blended or summed forces 1355 that direct the catheter and magnet 1318 "up" to and in between electrodes 1320, 1321.

Given that blood has a higher magnetic permeability than air, the magnetic field lines will be able to travel through the atrium more efficiently (and requiring less current to be passed through the wires) than if electrodes were simply located in air. Thus, sending up 1 amp of current through the wire wrapped about an electrode may efficiently create approximately 0.07 Tesla of magnetic force, which attracts the ablation catheter.

Given the size of the wire (e.g., 45 AWG) and the size of the current (e.g., 1 amp), one might expect energy (as described by $E=I^2/R$) to build up in the wire coils. However, due to the continuous pulsatile nature of blood flow through the heart, there may be sufficient energy dissipation provided to cool the coils or windings fast enough so there is no or little net gain of temperature for the coils or windings. Also, in varying embodiments different wire coatings (e.g., polyurethane, polyimide, polyester-imide) can allow for more efficient cooling as well.

As seen in FIGS. 8 and 9, various strategies exist for locating the windings around electrodes. In FIG. 8, the wire is wound along the length of the electrode. This would leave bottom 881 and top 882 of electrode 820 exposed. Thus, electrode 820 could take measurements (e.g., for mapping and/or verification of efficacy of ablation). Electrode 820 would not be directly connected with winding 841 that carries Im current 845. This "horizontal" winding would direct the magnetic field lines 847a-d towards the middle of the atrium if, for example, surface 881 was contacting the atrial wall. By varying the polarity of the current running through the wire, each individual electromagnet can be used to "push" or "pull" (i.e., reverse the direction of force 848) the ferromagnetic tip to the local region of interest for therapy.

In FIG. 9, the wire or wires is/are "vertically" wound along electrodes 920, 921. This configuration may minimize the width of the electrode and the customizations needed to be done to the original backbone of traditional basket catheters. By winding the wire "vertically" or perpendicular (i.e., perpendicular to the long axis of the electrodes shown in FIG. 9) along electrodes 920, 921, magnetic field lines 946, 947 may be directed along the length of the electrodes. The ferromagnetic catheter tip could ride along field lines that increase in strength with electrodes nearest the final region where ablation therapy is to be administered. Thus, the region where the catheter would be directed towards is where there was convergence between two adjacent electrodes whose current spin would be directed towards one another (i.e., clockwise and counter clockwise).

The strategies of "horizontal" and "vertical" wrapping could also be utilized together to maximize the ability of a guidance system to direct the therapy to the necessary region of the atrium. In various embodiments, all of the electromagnets, a small local portion of the electromagnets, or a single electromagnet would work together to guide the catheter tip. Each electromagnet winding can have its own current sink or all of them can sink to the same ground.

There are various embodiments for powering the windings. For example, a separate wire may be used for each electrode and a separate wire may be used for each winding such that voltage measurements can be taken from an electrode while the same electrode is being used as a core for the electromagnet. The separate wires can go around the electrodes as they feed to the next electrodes in the array. However, in an embodiment an electrode can be hollow to allow a wire or wires to pass through it while still allowing the electromagnetic windings to wind about the electrode (parallel or perpendicular to the alignment of each electrode).

In another embodiment, each electromagnetic winding may share a wire with an electrode adjacent to the electrode about which the winding is wound. For example, in FIG. 9 winding 941 for electrode 920 may connect to electrode 921. Setting the voltage of electrode 921 (e.g., positive or negative) will force current to run through winding 942 for electrode 921 in the desired direction, thereby creating the desired magnetic field. This "sharing" minimizes the surface area and the space required to wire each individual electromagnet winding.

In an embodiment, an ablation catheter may be modified so guiding the catheter magnetically is most efficient. For example, in FIG. 8 ablation tip 820' may be coated with a ferromagnetic alloy such as nickel, chromium oxide, iron, steel, and/or the like and serve as the magnet in addition to or in lieu of magnet 818. Ferromagnetic materials (e.g., iron, nickel, cobalt) may become magnetized in a magnetic field and retain their magnetism when the field is removed. Catheter tips coated with a ferromagnetic alloy will be ferromagnetic, have as good or better electrical conductivity as more traditional catheter tips, and be biocompatible in the time span that they would be in contact with the body. The ferromagnetic component may be the tip of the catheter (or tip region) where, for example, radiofrequency ablation therapy is conducted. However, a ferromagnetic component could be an insert into the shaft of the catheter near the tip allowing one to use traditional catheters that merely have the additional insert. In yet another embodiment, a ferromagnetic component could be a clip or addition that is attached near the end of a traditional ablation catheter so traditional RF catheters can be quickly adopted for use with embodiments of the invention.

In an embodiment, a permanent magnet may be placed in the catheter tip. In such an embodiment, the metal of the electrodes is not highly ferromagnetic. Thus, the magnet is still attracted to the induced magnetic fields instead of the metal cores of each of the electromagnets.

In yet another embodiment, magnetic paint may be painted around the edge of the ablation catheter tip. The magnetic paint may be around, but not on, the catheter tip. Thus, the paint would not inhibit the delivery of ablation energy (e.g., current) to the edge of the tip. As a result, ablation therapy is conducted in a typical fashion with typical energy amounts achieving typical tissue ablation depth. Various magnetic paints (e.g., Krylon 3151 Gray Magnet Spray Paint) impart ferromagnetic capabilities to metals that are not generally considered ferromagnetic.

Embodiments may also include paramagnetic materials (e.g., aluminum, platinum) that may become magnetized in a magnetic field but then lose the magnetism when the field is removed.

In another embodiment a small electromagnet may be placed on the interior of the RF ablation catheter. The electromagnet could be turned on and off by respectively supplying and removing current to the electromagnet. Doing so would allow the array of electromagnets and the catheter electromagnet to work together. Consequently, this would require less overall power to be supplied to both and increase the strength of the forces pulling the two together. For example, the electromagnet included in the catheter could be activated. The electromagnet in the array could also be activated such that the net electromagnetic fields for the array electromagnet and the catheter electromagnet could be aligned and complementary to facilitate navigation. In an embodiment the current to the electromagnet included in or coupled to the catheter could be reversed to change from "pulling" the catheter towards a magnetic field (e.g., a field produce by electrode 420 of FIG. 4) to "pushing" the catheter away from the same magnetic field.

In various embodiments, the magnetically attracted component (e.g., located in the ablation catheter) could be in the catheter tip so the magnetic guidance can directly move the tip to a specific region on the heart wall for therapy. However, in various embodiments the magnetically attracted component (e.g., located in the ablation catheter) could be near the catheter tip (e.g., proximal to the tip) so the magnetic guidance can move the tip to a general region for ablation so the user can manipulate the catheter as normal to complete therapy to the heart wall.

In an embodiment, to control the currents to the electromagnets each electromagnet may be connected in parallel to a switching card which is capable of connecting each electromagnet to a single DC current source. In other embodiments, AC current sources may be used. The proper amount of current (and proper polarity of current) can be delivered either through a current source or via a voltage source with a tunable potentiometer to regulate the amount of current to be delivered (which in turn may vary the force of the induce magnetic field and force exerted on the magnet of the steerable catheter). A system for use in delivering, recording, and generally working with current, voltage, and power is disclosed in FIG. 14, described below.

In an embodiment, the location for therapy is indexed to the specific electromagnets. Thus, the system can be automated (fully or partially) such that the device would merely need confirmation from the user (e.g., cardiologist, surgeon, doctor, medical practitioner) that the predicted site in need of therapy was indeed correct. In order to run the device one could merely feed in the witnessed pattern of the arrhythmia from previously run tests. The computer (e.g., FIG. 14) could analyze it and compare it to the current EKG and find where along the electrodes it is seeing that pattern. Then the system would know where to direct the catheter because the arrhythmia would already be indexed off of the same electromagnets it would use to guide it. For example, the system would know it needs to send the ablation catheter to location B 8-9 (i.e., spine B of basket catheter, between electrodes 8 and 9) because it has identified a specific or otherwise desirable electrophysiologic characteristic at that location. The system would then run a predetermined algorithm to guide the catheter from a known calibrated location directly to electrode B 8-9 and perform ablation until electrophysiologic testing and/or recording verifies abnormal activity (e.g., reentrant circuit) disappeared. The catheter can be directed towards specific locations by precalculated routines that turn some or all magnets on and off at specific magnetic powers at specific times to direct the catheter to a specific region. The sum of the forces on the catheter can be predicted through mathematical modeling such that the sum of the forces will equal out to a net force which will ultimately guide the catheter to the site of therapy.

In an embodiment, a user could manually determine the catheter needs to go to electrode C 9-10 by reading the signals from the electrodes. The user then activates the electromagnet at that site. The ablation catheter could then be drawn to the region of interest (e.g., near an electrode or electrodes that surround a pulmonary vein ostium). Since the signals read from the heart are indexed to the array of electromagnets the same way, one merely has to identify the location for therapy and tell the device to direct the catheter to that position. Once the catheter is in the correct position, micromanipulation can be performed by any other additional form including, but not limited to, manual manipulation leading to slight perturbations in the sum of the magnetic fields while still directing it to the original area overall.

Furthermore the magnetic field generated may be used not only to navigate the catheter but also to specify the amount of force placed by the catheter tip (since the catheter is close to or on the magnetically active electrode). This is addressed further below.

In another embodiment the magnetic intracardiac electrodes need not have any mapping properties (i.e., no need to sense electrical activity). If the electrodes have magnetic properties those properties can still be altered and used to navigate the ablation catheter within the cardiac chamber.

Figure 15:
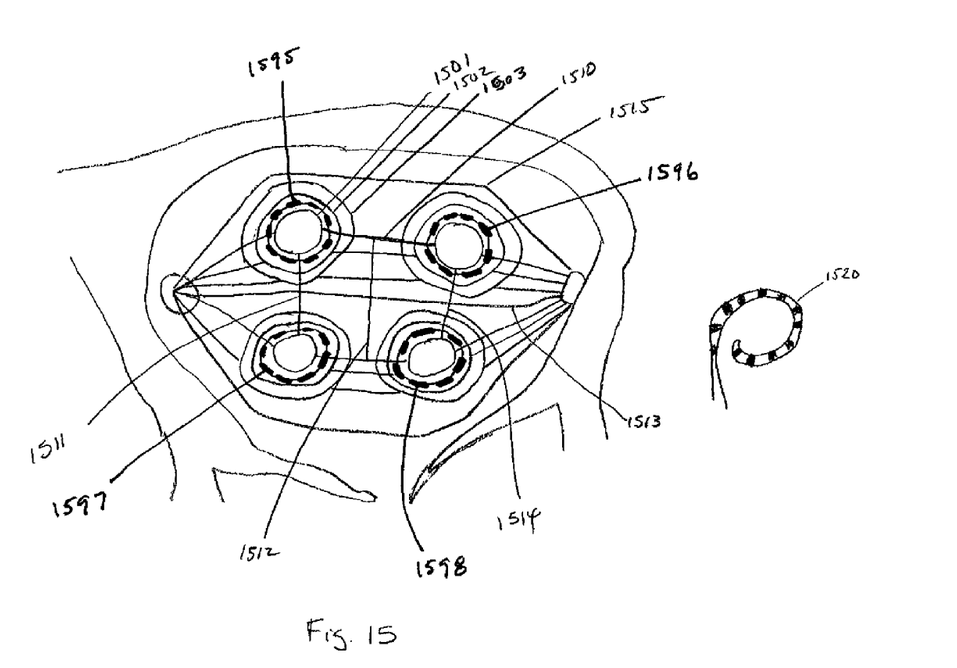
FIG. 15 includes a grid or mesh based catheter in an embodiment of the invention.

In still another embodiment, an array or meshwork of electrodes can fill a portion or all of a cardiac chamber. The array may include circular regions which go over the pulmonary vein ostia. FIG. 15 shows four ostia, each depicted with thick black dashed lines 1595, 1596, 1597, 1598. The basket includes four series of circular rings. The first series includes rings 1501, 1502, 1503. Ring 1501 is included in a region smaller than surrounding ostium 1595. Rings 1502, 1503 surround ostium 1595. The three other series of circular rings are similar and are not described in detail. Each ring may include various electrodes (not illustrated for simplicity). Each ring may couple to other rings via lengths or spines such as lengths 1510, 1511 for ring 1501. Thus, to treat an abnormal rhythm (e.g., atrial fibrillation) the user may guide an ablation catheter, such as ring catheter 1520 with electrodes located in a ring shape, to one of the rings such as ring 1501. Accounting for varying anatomies, the user may select to burn along an innermost ring for one ostium but along a second most interior ring for another ostium. By providing multiple series of rings the user can place the array one time and then just vary navigation sites (and thus ablation sites) by choosing which rings (and then magnetizing those rings) to use for navigation. Also, the user may guide the ablation catheter along various lengths between the various series. For example, burns may be made along lengths or struts 1511, 1512, 1513, 1514 (electrodes not illustrated for simplicity). Thus, an embodiment exists that allows magnetic navigation in the entire chamber (e.g., along strut 1515) and around the PV os (e.g., ring 1502).

While embodiments may include any number of series of rings, embodiments with four series of circular arrangements allow a user to isolate all four pulmonary veins. Afterwards, the user can make any number of linear lesions between or around the circular arrangements using electromagnetic guidance electrodes or devices found in the circular arrangements, on struts between the circular arrangements, or on other struts of the basket or mesh catheter. These burns could be made with little to no further manipulation of the basket catheter once the basket catheter's circular arrangements are positioned about the ostia.

Figures 16, 17:
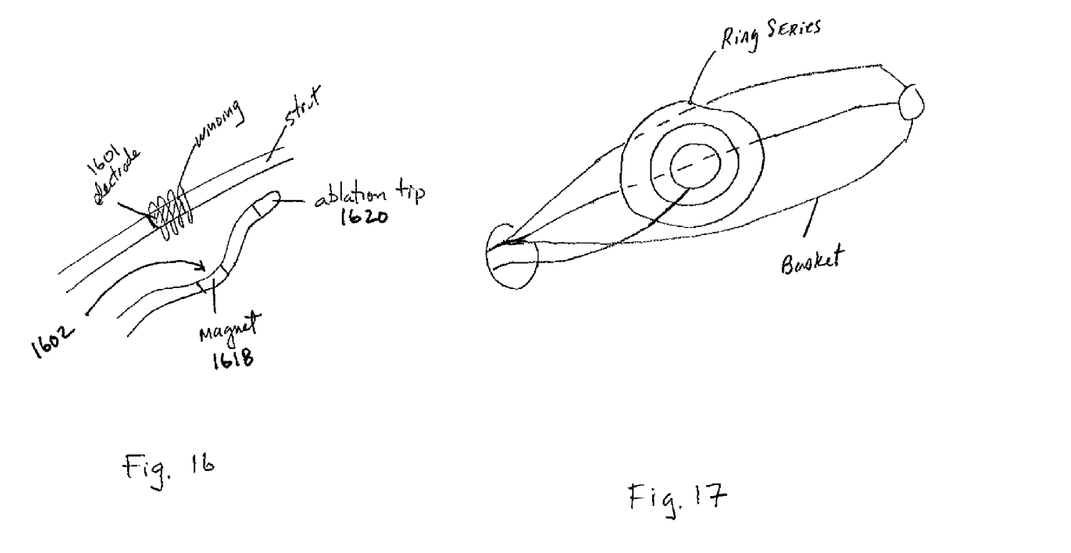
FIG. 16 includes a curved catheter in an embodiment of the invention.
FIG. 17 includes a ring based catheter in an embodiment of the invention.

FIG. 16 includes an embodiment wherein altering the magnetic field varies the attractive force exerted on the ablation catheter. By doing so, a user can control the contact force between the catheter tip and cardiac tissue. For example, if the user has an electrogram recording that is 3 milivolts at electrode 1601, the user can induce a field from electrode 1601 (using the surrounding winding as described above) to draw the ablation catheter near the electrode. The user could then ablate until a magnitude of less than 1 mv is recorded. However, if using high power energy delivery still does not result in the less than 1 mv goal, the user could increase the "attraction" exerted on the ablation catheter, thereby increasing the ablation catheter magnet's contact force with the magnetic mapping electrode. Doing so will naturally also increase the contact force exerted by the ablation catheter tip on surrounding cardiac tissue. This allows for a deeper burn.

As seen in FIG. 16, an embodiment of an ablation catheter may include bend or curve 1602 near or at ablation catheter magnet 1618. The bend may be configured so it can be made rigid after deployment into the heart. Thus, with a light attraction force exerted against the ablation catheter magnet (located along the curve) 1618 ablation tip 1620 (which is closer to the cardiac tissue than the magnet due to the bend or curve in the ablation catheter) would be near the tissue or against the tissue with limited force. However, with heavier attraction force exerted against the ablation catheter magnet the magnet may be fully pressed against the electromagnetic electrode of the basket catheter. Then, due to the curve in the catheter, the ablation tip would be firmly pressed against the tissue with increased force. Using the ablation catheter magnet as a pivot point, the ablation catheter could even be rotated by the user to thereby exert torque or rotational force against the ablation tip, thereby pushing the tip even harder against the tissue.

A method in an embodiment of the invention is now described. First, a target or candidate cardiac chamber is identified. Next, the mapping electrodes are delivered to the chamber via a sheath which may be introduced percutaneously (via needle access of the vascular system). The mapping electrode platform is deployed in a "low-profile", deflated, or any other geometric form so as to allow its manipulation and navigation through the lumen of sheath. Once it is guided to the chamber of interest it can be deployed to its geometrically desirable dimensions.

Next, the mapping electrodes comprise a series of electrodes arranged on a geometrically flexible platform. The platform creates a plurality of electrodes arranged in a two-dimensional (e.g., circular or flat surface) or three-dimensional manner. The platform allows for deployment of the electrodes so as to assure contact with cardiac tissue by a variety of means. These can include deployment by transfer of mechanical force from the proximal aspect of a sheath or catheter that is connected to the platform. Transfer of force leads to the electrode(s)' apposition to the target tissue. In this embodiment the operator confirms contact by fluoroscopic visualization (movement of the radioopaque electrodes with the cardiac cycle, geometric proximity to a known anatomic landmark) or by qualitative assessment of electrode signals (signal amplitude or voltage) or both.

In one embodiment the platform expands to the shape of the chamber or target geometry without the need for a custom-made platform of electrodes. In another embodiment scouting CT or MRI scans are performed in order to create custom platforms or assist in deployment of a generic platform. In yet another embodiment the platform consists of a series of flexible mesh-like wires which can be manipulated by the operator (with or without a second catheter) so as to localize specific areas. For example, in FIG. 17 a series of circular rings may be manipulated independently of a surrounding basket catheter. While the ring series is shown flat, it could be three dimensional and form, for example, a sphere upon expansion. There can be one or more circular arrangements (e.g., ring series) within the three dimensional framework.

An already described embodiment of the circular arrangement may, via catheter manipulation, be directed to the opening of the pulmonary vein (i.e., pulmonary vein (PV) os). The os is a known source of electrical impulses that lead to atrial fibrillation (AF). Because of this, delivery of ablative energy at the PV os can be important in performing AF ablations. In this embodiment once the circular aspect of the platform is placed on the os the ablation catheter can be magnetically navigated around the PV os, provided the circular aspect contains a plurality of magnetically active electrodes and the ablation catheter has a magnetically active tip (or tip region with a magnet placed proximal to the ablation tip).

In another embodiment multiple circular arrangements may exist within the platform. Each of these arrangements may be placed over a separate PV os (there are usually four of these in every heart). As the platform is comprised of a flexible mesh these circular or elliptical arrangements can be easily manipulated so as to place them over the target sites (PV os in this case).

In one embodiment, the circular arrangements are large enough to encircle more than one ostium. For example, in FIG. 15 each series surrounds a single ostium. However, an arrangement (e.g., circular, ovular, square, rectangular) could be large enough to surround two ostia. Burns could be made about the larger perimeter to thereby isolate two ostia at once. Of course, even larger perimeters could be made to encircle or encompass three or more ostia.

Once the circular/elliptical arrangements are in place the operator can have the ablation catheter tip be navigated to all regions of interest via the magnetic attraction between the catheter tip and electrodes. Furthermore in this and other embodiments linear or any other series of ablations can be delivered provided other electrodes in the platform are magnetically active. For example a linear lesion between two PV's (essentially connecting the two by a line of ablation lesions) can be created by navigating the ablation catheter along a series of magnetically active electrodes on the platform between the two veins. Once the platform is in place the remainder of all ablation deliveries can be performed by magnetic navigation of the ablation catheter via the magnetically active electrodes. Furthermore, the operator can assess the effects or efficacy of ablation by assessing any alterations in signal characteristics on the mapping or ablation electrodes. These effects may include a decrease in the electrogram amplitude or voltage.

Once the magnetically active electrodes are in position, the ablation catheter with its magnetically active tip (e.g., tip region) is introduced into the same chamber. As described herein embodiments of the invention allow navigation of the ablation catheter to all regions that contain magnetically active electrodes. The magnetically active electrodes allow not only geographic navigation of the ablation catheter to different areas, but may also provide for control of the force or tension generated by the catheter tip. It does so by, for example, adjusting the magnetic forces generated by the mapping electrodes, thus adjusting the forces between the ablation catheter and mapping electrode. The operator can use any criteria he or she wishes in making the necessary adjustments to any of the above variables. Once delivery of ablation lesions are completed the platform and ablation catheter are removed. The procedure is completed.

Figure 18:
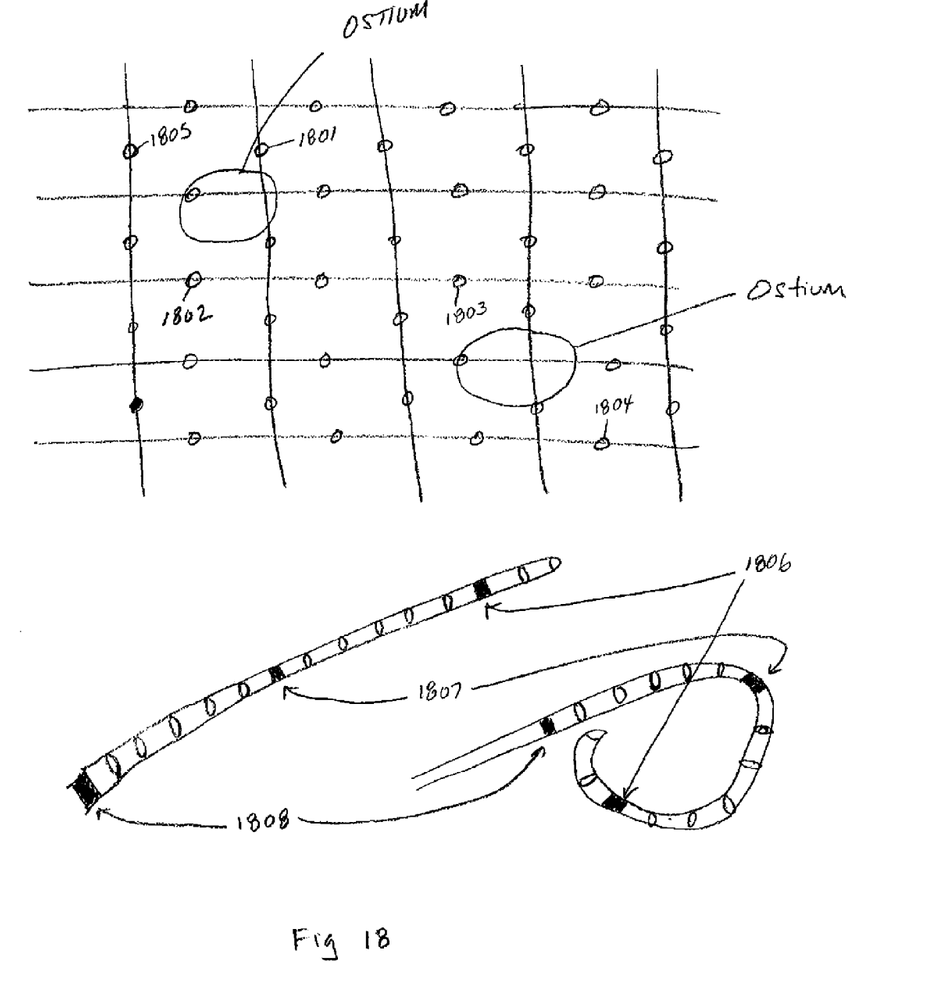
FIG. 18 includes a grid or mesh based catheter and an ablation catheter in an embodiment of the invention.

FIG. 18 includes a mesh, which could be included in a basket catheter, with electrodes (e.g., electrodes 1801, 1802, 1803, 1804, 1805) placed along its struts or spines. The user may deploy the mesh across the ostia. Once deployed, the user may determine which electrodes are near the ostia. For example, electrodes 1801 and 1802 happen in this instance to be on either side of a first ostium. The user may then introduce an ablation catheter having electrodes 1806, 1807, 1808. Electrodes 1806, 1807, 1808 may be paramagnetic or ferromagnetic in nature. Thus, a user could position the ablation catheter near electrodes 1801, 1802. Afterwards, the user could activate electrodes 1806, 1807 and electrodes 1801, 1802. With manipulation of the ablation catheter and attractive forces associated with electrodes 1801, 1802, 1806, 1807, a user may place electrode 1806 near electrode 1801 and electrode 1807 near electrode 1802 to thereby form a ring about ostium. Burns could then be made between other electrodes included on the ablation catheter. The same process could be repeated for other ostia. Consequently, the mesh array of electrodes allows the user to simply place the array in the chamber without regard (relatively speaking) to locating a specific electrode in a specific area. Instead, the user may determine which electrodes are of interest based on how the array falls across the ostia.

Additionally, other burns could be made. For example, electrode 1806 could be navigated near electrode 1805 and electrode 1808 could be navigated near electrode 1804. A linear burn could then be made along electrodes of the ablation catheter to thereby create a liner burn connecting the two ostia. Of note, taking the preceding linear burn scenario as an example, even if the distance between electrodes 1806 and 1808 is not long enough to span the distance between electrodes 1805 and 1804, the attractive forces between 1804 and 1808 and the attractive forces between 1806 and 1805 would still properly align the ablation catheter linearly between the two ostia.

Thus, in an embodiment an electrophysiologic system comprises a mapping catheter that includes a first mapping catheter electrode and a first mapping catheter winding. The winding may be wound around a portion of the first mapping catheter electrode but in other embodiments may be wrapped around another electrode or no electrode at all. The first mapping catheter may be suitable for transmitting electrophysiologic signals but may instead be used to deliver energy (e.g., radiofrequency energy or cryoablation energy). The system may further include a catheter, such as an ablation catheter, that includes a first ablation catheter magnet. When first current is supplied from a power supply to the first mapping catheter winding a first electric field is generated and exerts a first force on the first ablation catheter magnet to direct the first ablation catheter magnet towards a first anatomic location.

In an embodiment, the mapping catheter may include a second mapping catheter winding. When second current (which may or may not be of the same magnitude and/or polarity of the first current) is supplied to the second mapping catheter winding a second electric field is generated and exerts a second force on the first ablation catheter magnet to direct the second electrode towards the first anatomic location. The first and second currents may be supplied in series with one another, in parallel with one another, or completely independently of each other.

In an embodiment the mapping catheter includes a mesh having first and second struts arranged non-collinearly with each other and with the first strut including the first mapping catheter winding and the second strut including the second mapping catheter winding. For example, see electrodes 420, 421 of FIG. 4.

In an embodiment, the first force is included in a first vector and the second force is included in a second vector unequal to the first vector. A vector is a quantity having direction as well as magnitude. Thus, the direction and/or magnitude of the first vector may be unequal to the corresponding value of the second vector.

In an embodiment, the first and second forces are exerted simultaneously. For example, in FIG. 4 electrode 420 may be activated simultaneously or non-simultaneously with electrode 421. Simultaneously means the forces overlap in some form (e.g., fully and/or partially).

In an embodiment the first and second mapping catheter windings are both included in a single ring. For example, see FIGS. 12, 15, 17, and 18. The ring may be circular, rectangular, square, ovular, and the like. The ring may be monolithic or composed of various struts or lengths of material.

In an embodiment the first mapping catheter winding is wound in a first orientation and the second mapping catheter is wound in a second orientation rotated approximately 90 degrees from the first orientation. For example, one winding may be vertical (e.g., FIG. 9) and another may be horizontal (e.g., FIG. 8).

In an embodiment the first electric field may be stronger than the second electric field. Thus, one field may push or pull harder than the other field. This may be done simultaneously or non-simultaneously.

In an embodiment the first current is supplied to the first mapping catheter winding based on the electrophysiologic polarization signal. For example, when mapping reveals an electrode is near problematic tissue the electrode may be used to magnetically attract the ablation catheter.

In an embodiment the first mapping catheter winding is wound around a first portion of the first mapping catheter electrode but not around a second portion of the first mapping catheter electrode, the second portion configured to directly contact tissue to transmit the electrophysiologic polarization signal. For example, with FIG. 8 surfaces 881 and 882 are free to contact tissue directly.

In an embodiment when first current is supplied to the first mapping catheter winding via a first direction (positive polarity) the first electric field is generated in a first direction and when the first current is supplied to the first mapping catheter winding via a second direction (negative polarity) the first electric field is generated in a second direction unequal to the first direction.

In an embodiment the first force may direct the first ablation catheter magnet against tissue with a first level of force, and when second current, which is stronger than the first current, is supplied to the first mapping catheter winding a second electric field is generated and exerts a second force, which is stronger than the first force, on the first ablation catheter magnet to direct the first ablation catheter against tissue with a second level of force that is greater than the first level of force. The magnet may serve as a pivot point that may be used to pivot the ablation electrode more deeply and forcefully into tissue. In an embodiment the ablation catheter includes a first ablation electrode, configured to deliver ablation energy to tissue, which is noncollinear to the first ablation catheter magnet.

Various embodiments have been used in the context of the heart with a basket catheter. However, embodiments are not so limited and may include other types of catheters used in other locations. For example, a mesh catheter or a more traditional catheter with a single mapping electrode may still be used to record electrophysiologic signals, and then guide another catheter to the location where the signals were recorded. A basket catheter may facilitate ease of mapping within a chamber but the expandable electrode array is not necessary for practicing embodiments of the invention. Also, embodiments are useful in cardiac environments but may be used in other areas such as neurology. Embodiments are not limited to ablation contexts but more generally concern, for example, guiding a device within the body based on magnetism.

Figure 14:
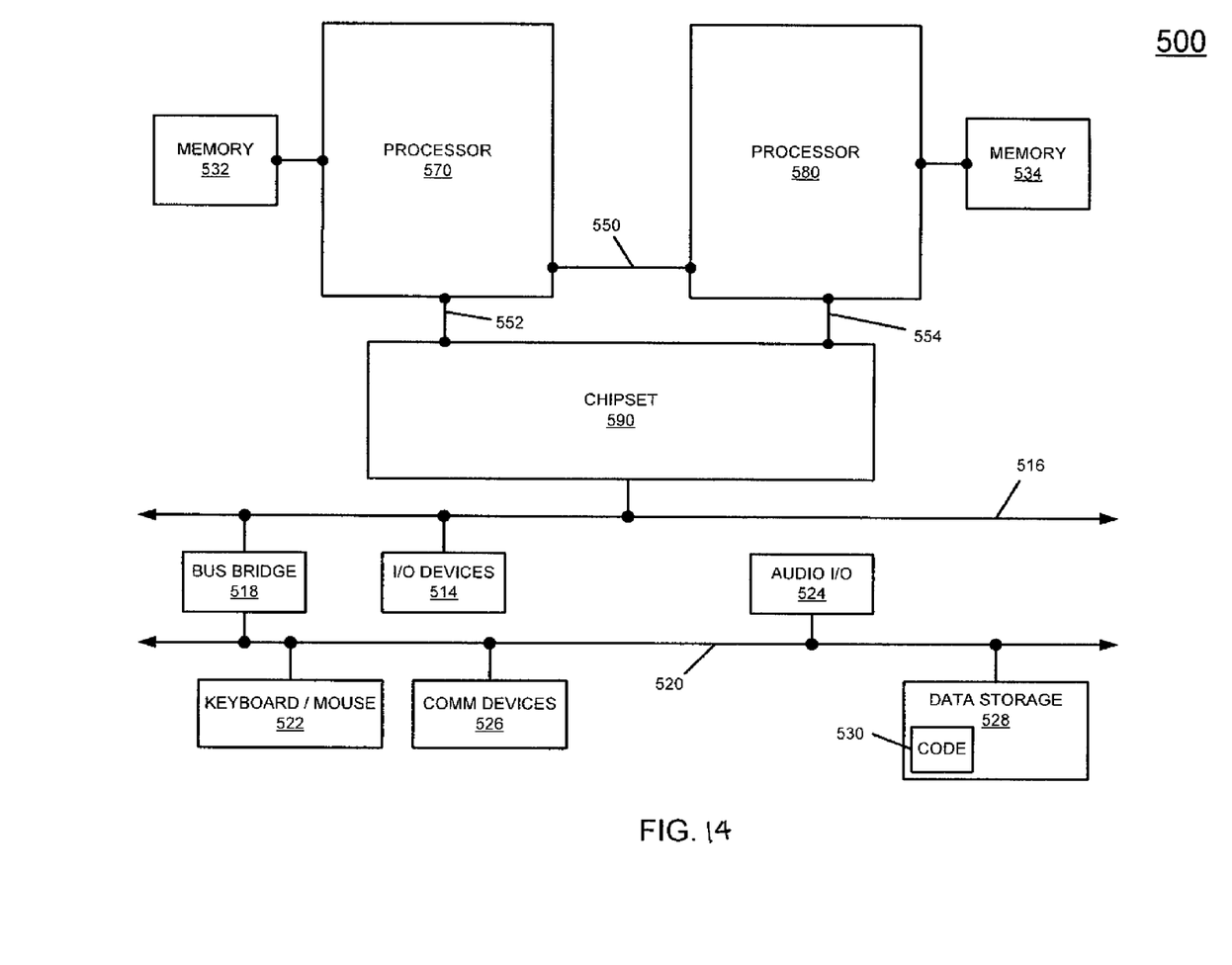
FIG. 14 includes a processor based system for implementing embodiments of the invention.

Embodiments may be implemented in many different system types. Referring now to FIG. 14, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multi-core processors. The term "processor" may refer to any device or portion of a device that processes electronic data from registers and/or memory to transform that electronic data into other electronic data that may be stored in registers and/or memory.

First processor 570 may include a memory controller hub (MCH) and point-to-point (P-P) interfaces. Similarly, second processor 580 may include a MCH and P-P interfaces. The MCHs may couple the processors to respective memories, namely memory 532 and memory 534, which may be portions of main memory (e.g., a dynamic random access memory (DRAM)) locally attached to the respective processors. First processor 570 and second processor 580 may be coupled to a chipset 590 via P-P interconnects 552, 554, respectively. Chipset 590 may include P-P interfaces.

Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An electrophysiologic system comprising:
a mapping catheter that includes a first mapping catheter electrode and a first mapping catheter winding; and
an ablation catheter that includes a first ablation catheter magnet;
wherein when a first current is supplied from a power supply to the first mapping catheter winding a first electric field is generated and exerts a first force on the first ablation catheter magnet to direct the first ablation catheter magnet towards a first anatomic location;
wherein the first mapping catheter winding is wound around a portion of the first mapping catheter electrode.

2. The system of claim 1 wherein the mapping catheter includes a second mapping catheter winding and when a second current is supplied to the second mapping catheter winding a second electric field is generated and exerts a second force on the first ablation catheter magnet to direct the first ablation catheter magnet towards the first anatomic location.

3. The system of claim 2 wherein the mapping catheter includes a mesh having first and second struts arranged non-collinearly with each other and with the first strut including the first mapping catheter winding and the second strut including the second mapping catheter winding.

4. The system of claim 2 including the power supply, wherein the power supply is configured to supply the first current and the second current such that the first force is included in a first vector and the second force is included in a second vector unequal to the first vector.

5. The system of claim 2 including the power supply, wherein the power supply is configured to supply the first current and the second current such that the first and second forces are exerted simultaneously.

6. The system of claim 2 wherein the first and second mapping catheter windings are both included in a single ring.

7. The system of claim 2 wherein the first mapping catheter winding is wound in a first orientation and the second mapping catheter winding is wound in a second orientation rotated approximately 90 degrees from the first orientation.

8. The system of claim 2 including the power supply, wherein the power supply is configured to supply the first current and the second current such that the first electric field is stronger than the second electric field.

9. The system of claim 2 wherein (a) the first ablation catheter magnet includes a material selected from the group consisting of a paramagnetic material, electromagnetic material, and ferromagnetic material, (b) the mapping catheter is not coupled to the ablation catheter, and (c) the first and second forces are exerted non-simultaneously.

10. The system of claim 1 wherein the first mapping catheter electrode is configured to transmit an electrophysiologic polarization signal.

11. The system of claim 10 including the power supply, wherein the power supply is configured to supply the first current such that the first current is supplied to the first mapping catheter winding based on the electrophysiologic polarization signal.

12. The system of claim 10 wherein the first mapping catheter winding is wound around a first portion of the first mapping catheter electrode but not around a second portion of the first mapping catheter electrode, the second portion configured to directly contact tissue to transmit the electrophysiologic polarization signal.

13. The system of claim 1 including the power supply, wherein the power supply is configured to supply the first current such that when the first current is supplied to the first mapping catheter winding via a first direction the first electric field is generated in an additional first direction and when the first current is supplied to the first mapping catheter winding via a second direction the first electric field is generated in an additional second direction unequal to the additional first direction.

14. The system of claim 1 including the power supply, wherein the power supply is configured to (a) supply the first current such that the first force is to direct the first ablation catheter magnet against tissue with a first level of force, and (b) supply a second current, which is stronger than the first current, to the first mapping catheter winding such that a second electric field is generated and exerts a second force, which is stronger than the first force, on the first ablation catheter magnet to direct the first ablation catheter magnet against the tissue with a second level of force that is greater than the first level of force.

15. The system of claim 14, wherein the ablation catheter includes a first ablation electrode configured to deliver ablation energy to the tissue.

16. The system of claim 1 including the power supply, wherein the power supply is configured to supply the first current to the first mapping catheter winding via a first cable that passes through a first aperture included in the first mapping catheter electrode.

17. An electrophysiologic system comprising:
a mapping catheter that includes a first mapping catheter electrode and a first mapping catheter winding; and
an ablation catheter that includes a first ablation catheter magnet;
wherein when a first current is supplied from a power supply to the first mapping catheter winding a first electric field is generated and exerts a first force on the first ablation catheter magnet to direct the first ablation catheter magnet towards a first anatomic location;

wherein the first mapping catheter electrode is configured to transmit an electrophysiologic polarization signal;

wherein the first mapping catheter winding is wound around a first portion of the first mapping catheter electrode but not around a second portion of the first mapping catheter electrode, the second portion configured to directly contact tissue to transmit the electrophysiologic polarization signal.

18. The system of claim 17 including the power supply, wherein the power supply is configured to supply the first current such that when the first current is supplied to the first mapping catheter winding via a first direction the first electric field is generated in an additional first direction and when the first current is supplied to the first mapping catheter winding via a second direction the first electric field is generated in an additional second direction unequal to the additional first direction.

19. The system of claim 17 wherein the mapping catheter includes a second mapping catheter winding and when a second current is supplied to the second mapping catheter winding a second electric field is generated and exerts a second force on the first ablation catheter magnet to direct the first ablation catheter magnet towards the first anatomic location.

* * * * *